US006652552B2

(12) United States Patent
DuMontelle (10) Patent No.: US 6,652,552 B2
(45) Date of Patent: Nov. 25, 2003

(54) ACTUATING HANDLE FOR A SURGICAL INSTRUMENT (75) Inventor: Jeffrey P. DuMontelle, Irvine, CA (US)

(73) Assignee: RKL Technologies, Inc., Corona, CA (US)

(*) Notice: Subject to any disclaimer, the term of this patent is extended or adjusted under 35 U.S.C. 154(b) by 0 days.

(21) Appl. No.: 09/912,763

(22) Filed: Jul. 25, 2001

(65) Prior Publication Data

US 2003/0023258 A1 Jan. 30, 2003

(51) Int. Cl.[7] .............................................. A61B 17/32
(52) U.S. Cl. ....................................... 606/184; 606/185
(58) Field of Search ................................. 606/159, 167, 606/184, 185; 294/100

(56) References Cited

U.S. PATENT DOCUMENTS

| 1,018,065 | A | * | 2/1912 | Marble | 294/100 |
|---|---|---|---|---|---|
| 1,616,121 | A | | 2/1927 | Gruber | |
| 2,137,710 | A | | 11/1938 | Anderson | |
| 2,518,994 | A | | 8/1950 | Miller | |
| 2,989,334 | A | | 6/1961 | Browne | |
| 3,146,015 | A | | 8/1964 | Roberge | |
| 3,265,429 | A | | 8/1966 | Shatt | |
| 3,774,438 | A | * | 11/1973 | Weston | 606/142 |
| 3,776,237 | A | | 12/1973 | Hill et al. | 128/305 |
| 4,005,897 | A | * | 2/1977 | Smith | 294/115 |
| 4,018,228 | A | * | 4/1977 | Goosen | 606/184 |
| 4,216,776 | A | | 8/1980 | Downie et al. | 128/305 |
| 5,002,554 | A | | 3/1991 | Korber | 606/174 |
| 5,009,661 | A | | 4/1991 | Michelson | 606/170 |
| 5,089,007 | A | | 2/1992 | Kirsch et al. | 606/205 |
| 5,129,913 | A | | 7/1992 | Ruppert | 606/184 |
| 5,192,294 | A | | 3/1993 | Blake, III | 606/184 |
| 5,282,817 | A | | 2/1994 | Hoogeboom et al. | 606/167 |
| 5,341,965 | A | | 8/1994 | Maas et al. | 222/340 |
| 5,613,950 | A | * | 3/1997 | Yoon | 604/105 |
| 5,910,153 | A | | 6/1999 | Mayenberger | 606/184 |
| 6,162,209 | A | | 12/2000 | Gobron et al. | 606/1 |
| 6,176,867 | B1 | | 1/2001 | Wright | 606/184 |

* cited by examiner

Primary Examiner—Michael J. Milano
Assistant Examiner—Bradford C Pantuck
(74) Attorney, Agent, or Firm—Cohen & Sakaguchi LLP (57) ABSTRACT A handle and methods for its use are provided for actuating surgical components such as blades, clamps, punches, needles, shears, etc., primarily for use in cardiovascular or arthroscopic surgery. The handle is a single-piece handle, including an outer portion and an inner portion. The inner portion is substantially within the outer portion, and includes an actuating component, and a guiding component connected to the actuating component. The actuating component includes a finger grip, and a spring force component which biases the finger grip and the guiding component to extend and towards a distal tip of the neck. A stress limiting component limits stress at a critical point of the spring force component by limiting movement of the spring force component at the critical point during actuation of the actuating component. The guiding component is adapted for movement along a longitudinal axis of the handle, in response to actuation and release of the actuating component, thus allowing a surgical component connected to a distal tip of the guiding component to function.

29 Claims, 6 Drawing Sheets

ACTUATING HANDLE FOR A SURGICAL INSTRUMENT

FIELD OF THE INVENTION

The present invention relates generally to surgical instruments, and more particularly to an actuating handle for actuating a surgical component such as a blade, clamp, punch, needle, shear, etc., and methods of using same.

BACKGROUND OF INVENTION

The contents of each of the U.S. patents and other references, if any, cited in this Background Of Invention section, are hereby incorporated herein by reference.

In surgery, incisions or openings are often needed to provide access for surgical or diagnostic instruments, implantation of bioprosthetic devices, attachment points for autologous or xenographic tissues, or for other reasons. Typically, instruments used for creating such openings include a handle and/or actuating component constructed of many mechanical parts, thus increasing the complexity of manufacture, assembly, use, and maintenance and, in some cases, decreasing the durability and reliability of the instrument.

Examples of such surgical instruments with multiple-part handles or actuating components are described in the following United States patents: U.S. Pat. No. 3,776,237 issued Dec. 14, 1973 to Hill; U.S. Pat. No. 4,018,228 issued Apr. 19, 1977 to Goosen; U.S. Pat. No. 4,216,776 issued Aug. 12, 1980 to Downie et al; U.S. Pat. No. 5,192,294 issued Mar. 9, 1993 to Blake III; and U.S. Pat. No. 6,176,867 issued Jan. 23, 2001 to Wright. Each of these describe handles or actuating components which use a coil spring to create a spring force which biases the operative portion of the instrument to an original position, and which assists in actuating the instrument.

Further examples of such surgical instruments with multiple-part handles or actuating components are described in the following United States patents: U.S. Pat. No. 5,002,554 issued Mar. 26, 1991 to Korber; U.S. Pat. No. 5,282,817 issued Feb. 1, 1994 to Hoogeboom et al; and U.S. Pat. No. 5,910,153 issued Jun. 8, 1999 to Mayenberger. Each of these describe handles or actuating components which use separate bowed elements such as metal arms which are used to actuate the surgical component.

U.S. Pat. No. 5,089,007 issued Feb. 18, 1992 to Kirsch et al, describes a surgical instrument having a body formed of a single length of flexible steel, combined with a collet. However, the body must be stamped, then bent and welded together to form a handle. Furthermore, the actuating mechanism requires squeezing opposing bowed metal elements of the body together in a manner similar to operation of a tweezers, and thus may require extraordinary dexterity to maintain a proper and secure grip of the instrument while in use. The handle described in Kirsch is also adapted to function only with a collet responsive to camming surfaces at the forward portion of the collet.

Accordingly, there is a need for surgical instrument actuating handle manufactured as a single-piece, such as from machining or molding, which includes an actuating component and has an ergonomic design contributing to a secure and controllable grip.

SUMMARY

The present invention describes a surgical handle for actuating surgical components such as blades, clamps, punches, needles, shears, etc., primarily for use in cardiovascular or arthroscopic surgery. The handle is a single-piece handle, including an outer portion and an inner portion. The outer portion is defined by a head and a neck. The inner portion is substantially within the outer portion, and includes an actuating component, and a guiding component connected to the actuating component. The actuating component includes a finger grip, and a spring force component which biases the finger grip and the guiding component to extend away from the head and towards a distal tip of the neck. A stress limiting component limits stress at critical points of the spring force component by limiting movement of the spring force component at the critical points during actuation of the actuating component. The guiding component is adapted for movement through the neck of the outer portion along a longitudinal axis of the neck, in response to actuation and release of the actuating component, thus allowing a surgical component connected to a distal tip of the guiding component to function.

The single-piece construction of the handle decreases the complexity of manufacture and maintenance. The ergonomic finger grip contributes to a secure and comfortable grip, and allows for controlled actuation of the actuating component with only a single hand. The handle may be manufactured in various dimensions as necessary for a particular function, but a single handle is adapted to receive a variety of surgical components.

Further objects and advantages of the present invention are discussed in the detailed description that follows.

DETAILED DESCRIPTION

The present invention describes a surgical handle for actuating surgical components such as blades, clamps, punches, needles, shears, etc., primarily for use in cardiovascular or arthroscopic surgery. The handle is a single-piece handle, and includes an actuating component having a finger grip and a spring force component. A stress limiting component limits stress at critical points of the spring force component by limiting movement of the spring force component at the critical points during actuation of the actuating component. Actuation of the actuating component causes a guiding component to move along a longitudinal axis of the handle, thus allowing a surgical component connected to a distal tip of the guiding component to function in a desired manner.

Figure 1:
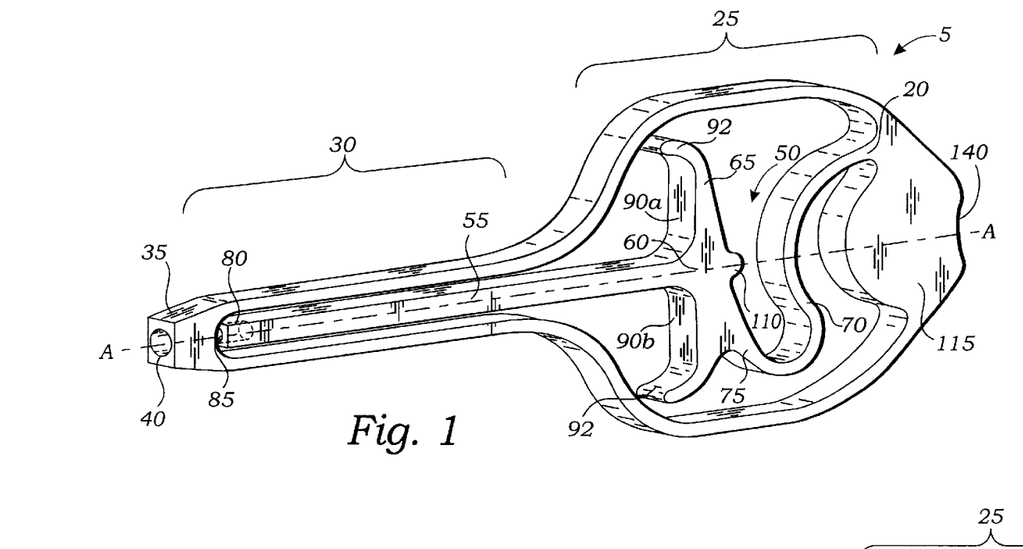
FIG. 1 is a perspective view of a preferred embodiment of an actuating handle in accordance with the present invention.
Figure 2:
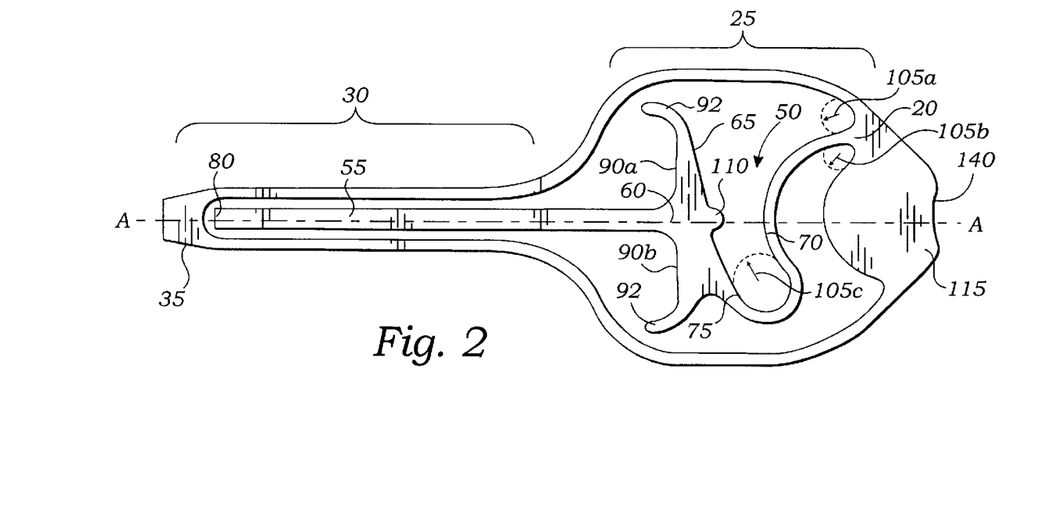
FIG. 2 is a planar view of the actuating handle of FIG. 1, with the spring force component in a natural bias position, and with the guiding component in a correspondingly extended position.
Figure 3:
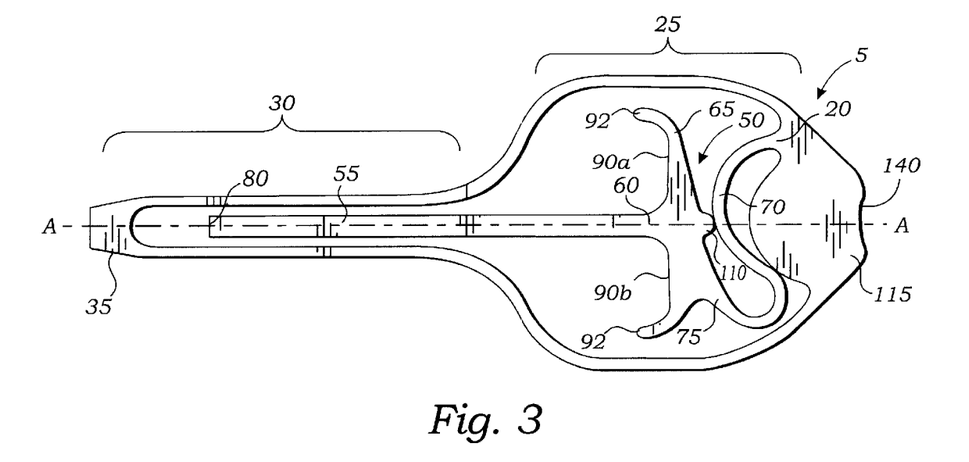
FIG. 3 is a planar view of the actuating handle of FIG. 1, with the with the spring force component compressed, and the guiding component in a correspondingly retracted position.

Turning to FIG. 1, a perspective view of a preferred embodiment of the actuating handle 5 in accordance with the present invention is shown. Handle 5 is a single-piece object as best seen in FIGS. 1–3. That is, handle 5 may be machined or stamped from a single block or sheet of material, molded from a single mold cavity, cast from a single mold, etc., to produce the final object. No additional parts are required. No additional welding, bending, or other process is required to shape handle 5 or any portions thereof. The material may be surgical-grade steel, titanium, other metals known in the art, polycarbonate, polyvinyl chloride, acetyl, styrene or other types of plastic.

Figure 4:
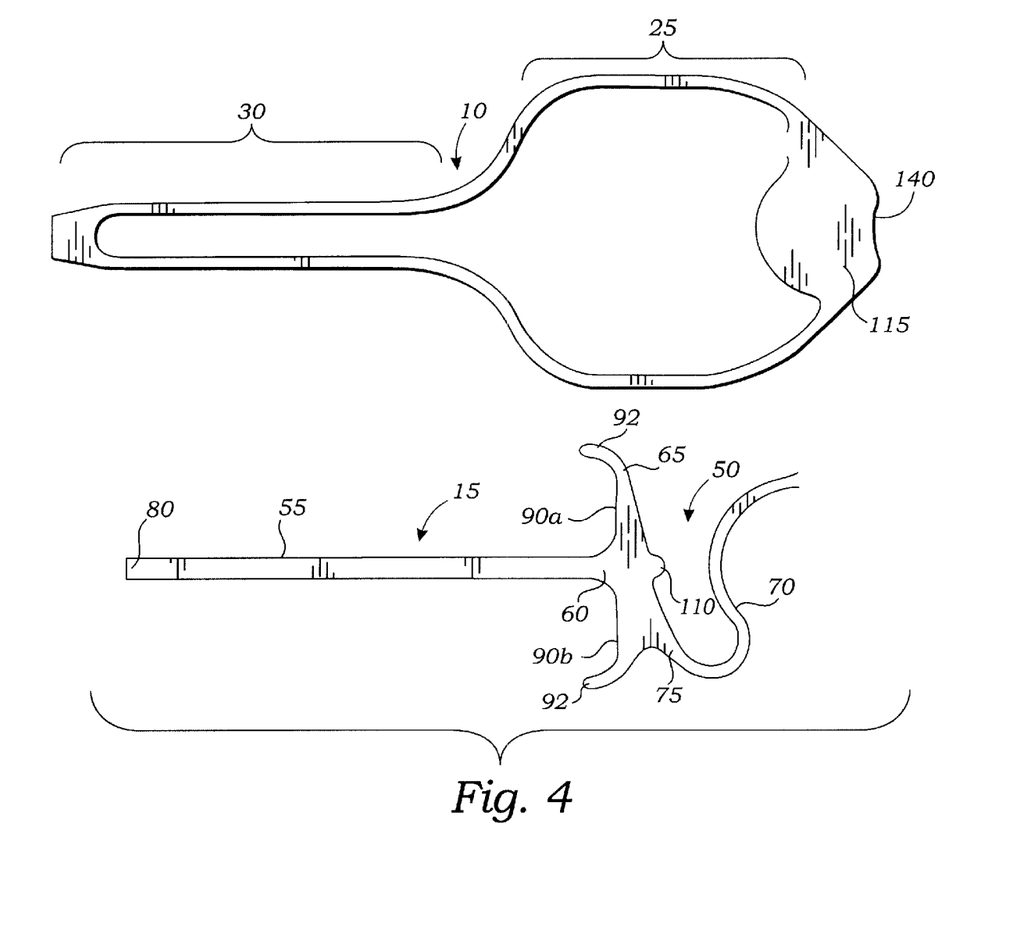
FIG. 4 shows planar views of the inner and outer portions of the handle of FIG. 1, separated for illustration purposes only, to illustrate the distinction between the two various portions.

Handle 5 has an outer portion 10 and an inner portion 15 (as best seen in FIG. 4) which merge into each other at a first merge location 20. The terms outer portion 10 and inner portion 15 are used to describe various portions of handle 5 relative to each other, and first merge location 20 is thus not an exact point, but rather a reference area which identifies the separation of the defined outer portion 10 from the defined inner portion 15. Inner portion 15 is positioned substantially within outer portion 10, as seen in FIGS. 1–3, and preferably lies substantially within the same plane as outer portion 10.

Figure 7:
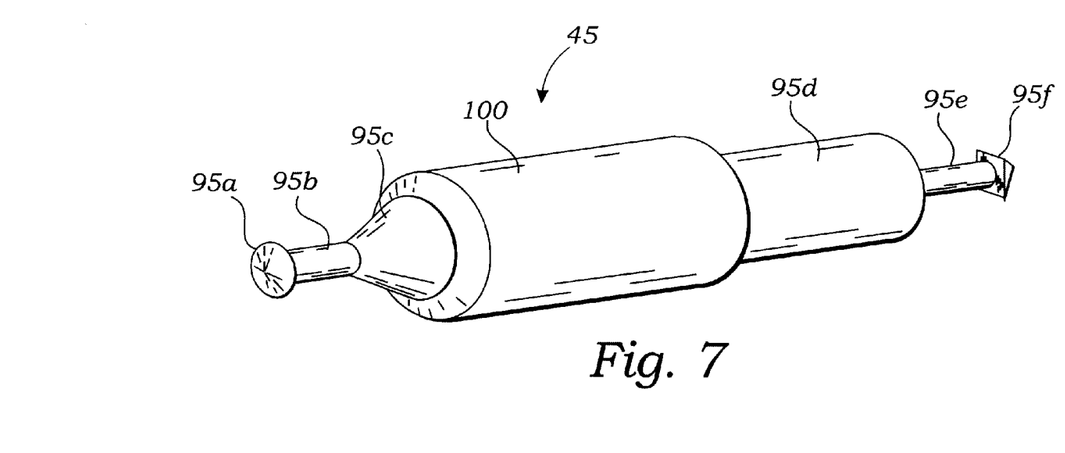
FIG. 7 is a close-up perspective view of the surgical component seen in FIGS. 5 and 6.

Outer portion 10 comprises a head 25 and a neck 30, these terms also being used to describe various portions of handle 5 relative to each other, and thus there are no exact points which separate head 25 from neck 30, but rather head 25 and neck 30 merge into each other to together form outer portion 10 of handle 5. Neck 30 terminates at a distal tip 35 having an opening 40. Opening 40 is adapted to receive a surgical component 45 as described in more detail herein, an example of which is shown in FIG. 7. Opening 40 may be a bore hole or combination of counter bored hole and bore hole, as seen in FIG. 1, or another type of opening for receipt of a specific class of surgical components 45. For example, opening 40 may be a slit (not shown) located on the underside of distal tip 35, for receipt of an elongate blade or cutting wheel (not shown).

Inner portion 15 comprises an actuating component 50 and a guiding component 55. Actuating component 50 merges into guiding component 55 at a second merge location 60, which also is not an exact point, but rather a reference area which identifies the separation of actuating component 50 and guiding component 55. From a planar perspective, (e.g., referring to the planar view of outer portion 10 as seen in FIG. 4), and considering outer portion 10 to be a substantially closed geometric figure, inner portion 15 is positioned substantially within the borders of outer portion 10 and substantially within the same plane of outer portion 10, as seen in FIGS. 1–3.

Actuating component 50 comprises a finger grip 65 and a spring force component 70, which merge into each other at a third merge location 75. Third merge location 75 also is not an exact point, but rather a reference area which identifies the separation of finger grip 65 and spring force component 70. In the embodiment shown in the drawings, first merge location 20 and third merge location 75 thus define opposing terminal ends of spring force component 70.

Guiding component 55 extends longitudinally along longitudinal axis A—A, through the support structure created by neck 30, and terminates at a distal tip 80 which is adapted to receive a surgical component 45. For example, distal tip 80 of guiding component 55 may have an opening 85 such as a counter-bore hole as seen in FIG. 1, corresponding to bore hole 40 at distal tip 35 of neck 30. Or, for example, distal tip 80 of guiding component 55 may have a slit (not shown) corresponding to a slit (not shown) at distal tip 35 of neck 30 as previously described. Thus, a surgical component 45 may be secured in multiple locations, such as in opening 85 and opening 40. Various methods of attachment of various surgical components 45 are known in the art, which use combinations of friction, wedging, snapping, or other mating mechanisms. A sample surgical component 45 is seen in FIG. 7, and is discussed in more detail herein.

Figure 5:
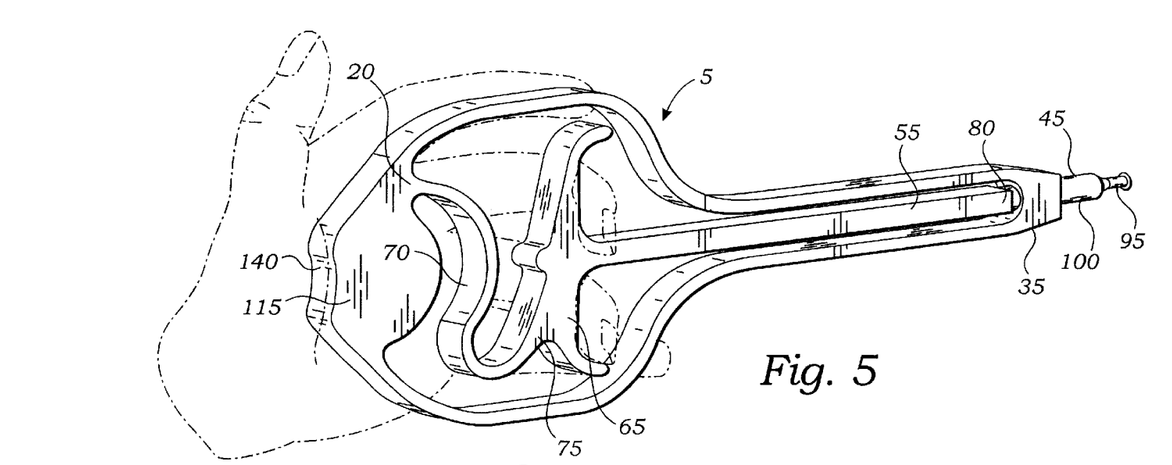
FIG. 5 shows the actuating handle of FIG. 1, with the guiding component in an extended position, and in combination with a surgical component connected to the distal tip of the guiding component. A hand is drawn in phantom to illustrate a method of gripping the handle.
Figure 6:
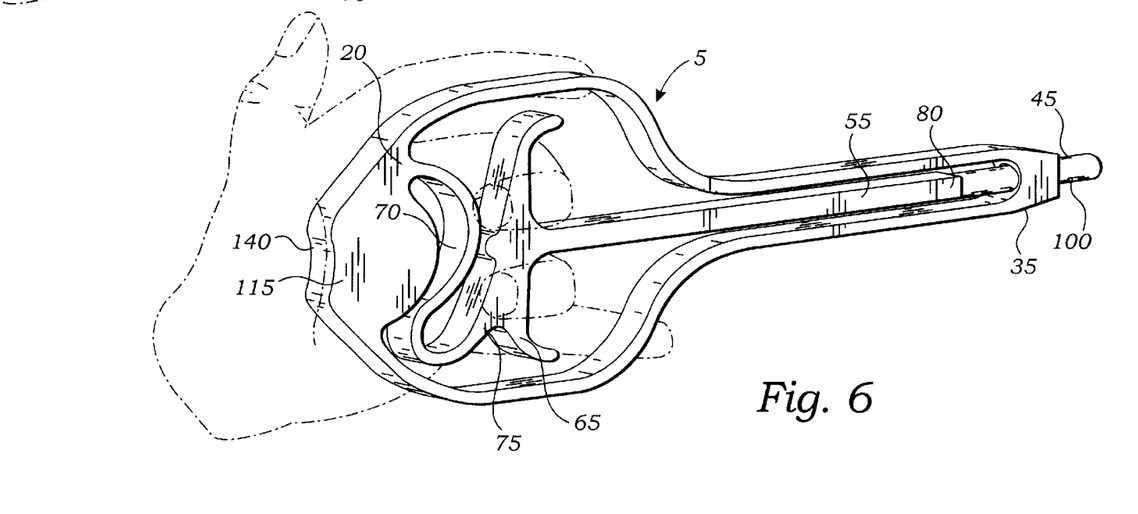
FIG. 6 shows the actuating handle and surgical component of FIG. 4, with the guiding component in a retracted position.

Referring back to actuating component 50, finger grip 65 and spring force component 70 will now be described in more detail. Finger grip 65 includes contact surfaces 90a and 90b (FIGS. 1–4), for gripping (as seen in FIGS. 5 and 6) by a person using handle 5, and may also include anti-slip guards 92 to limit the vertical relative movement of the fingers. Anti-slip guards 92 may take alternative forms, such as loops, and finger grip 65 may include additional anti-slip features such as texturing on contact surfaces 90a, 90b, or concave indentations on contact surfaces 90a, 90b for further securing fingers.

Spring force component 70 is biased to force guiding component 55 towards distal tip 35 of neck 30, as seen in FIGS. 2 and 5. When spring force component 70 is compressed by manipulating finger grip 65 in a retracted direction to oppose the natural bias force of spring force component 70, guiding component 55 correspondingly retracts along axis A—A, as seen in FIGS. 3 and 6. The force required to compress spring force component 70 to various degrees may depend on the thickness and/or length thereof, or on the type of material used to create handle 5. Thus, various models of handle 5 may be manufactured to suit various surgical or other needs.

With a surgical component 45 attached to distal tip 80 of guiding component 55, a moveable portion 95 of surgical component 45 correspondingly retracts with retraction of finger grip 65, and thus moves in synch with guiding component 55 substantially along axis A—A upon actuation and release of actuating component 50. This is best seen by comparing FIG. 5 to FIG. 6, in which moveable portion 95 of vessel punch 45 is initially biased by spring force component 70 to extend through a non-moveable portion 100 of vessel punch 45, and is retracted upon retraction of finger grip 65. (The surgical component 45 illustrated in the drawings is a vessel punch shown in more detail in FIG. 7, in which various parts of the moveable portion are labeled 95a, 95b, 95c, 95d, 95e, and 95f respectively, and referred to collectively herein as moveable portion 95.) Release of actuating component 50 (e.g., by allowing spring force component 70 to decompress), causes guiding component 55 to extend back to its initially biased position. Thus, actuation and release of actuating component 50 each cause guiding component 55 to move longitudinally substantially along axis A—A in retracted and extended directions respectively. Non-moveable portion 100 of surgical component 45 may extend through opening 40 at distal tip 35 of neck 30.

In a preferred embodiment as seen in the drawings, spring force component 70 is a dual-curved structure as seen in the drawings, having radii of curvature 105a, 105b, 105c adjacent first and third merge locations 20 and 75 respectively, as designated by arrows in FIG. 2. Corresponding dashed-lined circles are shown for illustration to clarify the defined radii 105a, 105b, and 105c. Critical "points" of spring force component 70 are at first and third merge locations 20, 75, in which spring force component 70 experiences the most stress during compression. Spring force component 70 is thus fashioned with radii 105a, 105b, 105c determined empirically based upon the material used, such that during compression (e.g., actuation of actuating component 50) the movement of spring force component 70 at the critical points is limited such that none of the radii 105a, 105b, 105c associated therewith reach a corresponding critical radius at which the material would crack, break, or unacceptably fatigue.

For example, it is well-known in the art that bending moments cause tension and compression stress in beams. If the tension or compression stress exceeds the strength of the material, the material will generally crack and then break. Typical unfilled polycarbonate plastic has an ultimate tensile strength of approximately 72 mega-pascals and an ultimate compression strength of approximately 86 mega-pascals. A bend that produces tension or compression exceeding these limits will cause the material to fail. In a preferred embodiment of the present invention, the thickness of the spring force component 70 and the desired travel of the guiding component 55 require any of the minimum critical radii (105a, 105b, or 105c) for the handle should be greater than 0.125 inches and preferably greater than 0.200 inches. Based on the relative strength of other materials, the critical radius may be made smaller or larger to ensure good fatigue life.

To further ensure the critical radii 105 are not violated, a stress limiting component 110 is positioned to limit stress at the critical points. In a preferred embodiment, stress limiting component 110 is a bump protruding/extending from finger grip 65, as seen in FIGS. 1–3. When actuating component 50 is actuated to a certain degree, stress limiting component 110 contacts spring force component 70, as seen for example in FIGS. 3 and 6. The degree of compression at which this occurs is referred to herein as a position of maximum actuation. Spring force component 70 may also contact the heel 115 of handle 5 during maximum actuation, as seen also in FIGS. 3 and 6, to further limit the degree to which spring force component 70 can be compressed and the degree to which radii 105 may be altered (e.g., increased or decreased as the case may be).

Stress limiting component 110 may also be implemented in other manners. For example, a bump or rod may extend from spring force component 70 or head 25, or teeth (not shown) may extend at an angle from anti-slip guards 92 to mate with slits (not shown) in the undersurface head 25. The specific implementation of stress limiting component 110 is not critical. The point is that a feature such as stress limiting component 110 is desirable to limit movement of spring force component 70 at a critical point during actuation of actuating component 50 such that a radius of curvature 105 associated with the critical point does not reach a critical radius.

Throughout this application, references are made to actuating the actuating component 50. Further references are to actuating, retracting, forcing, or otherwise manipulating finger grip 65, and to actuating or compressing spring force component 70. It should be understood that reference to actuating the actuating component 50 are general references, whereas references to actuating finger grip 65 or spring force component 70 are more specific based on the specific embodiments shown and described. All such references are in the context of causing guiding component 55 to move correspondingly with the actuation described.

As an alternate way of describing the structure of handle 5, we can traverse a planar view of handle 5 from distal tip 80 of guiding component 55, all the way around, to illustrate the geometric continuity of an embodiment of handle 5 as shown and described herein. This can be done, for example, with a pencil using FIG. 2, and never lifting the pencil from the paper. Referring back then to FIG. 2, and arbitrarily beginning at distal tip 80 of guiding component 55, we traverse along guiding component 55 towards finger grip 65 which bifurcates into anti-slip guards 92. We then continue down finger grip 65 past stress limiting component 110 through dual curves of spring force component 70, to first merge location 20. We continue then downward through heel 115, bottom edge of head 25 and bottom edge of neck 30, to distal tip 35 of neck 30, across upper edge of neck 30 then head 25, and back to first merge location 20. This aforementioned exercise should further clarify the single-piece aspect of handle 5.

Figure 8A:
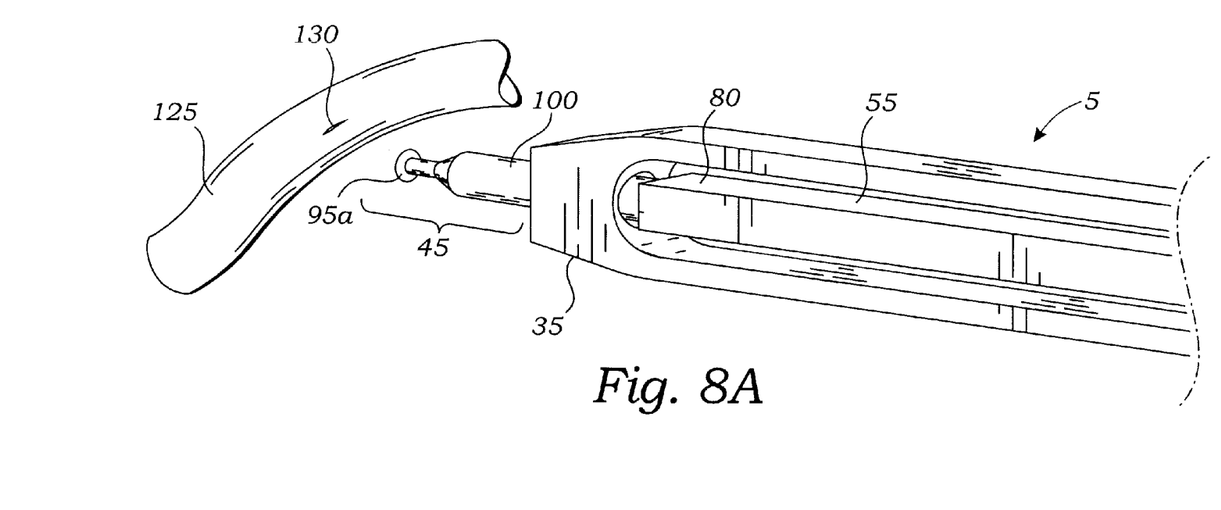
FIG. 8A shows the actuating handle and surgical component of FIG. 5 in position for use on a vessel.
Figure 8B:
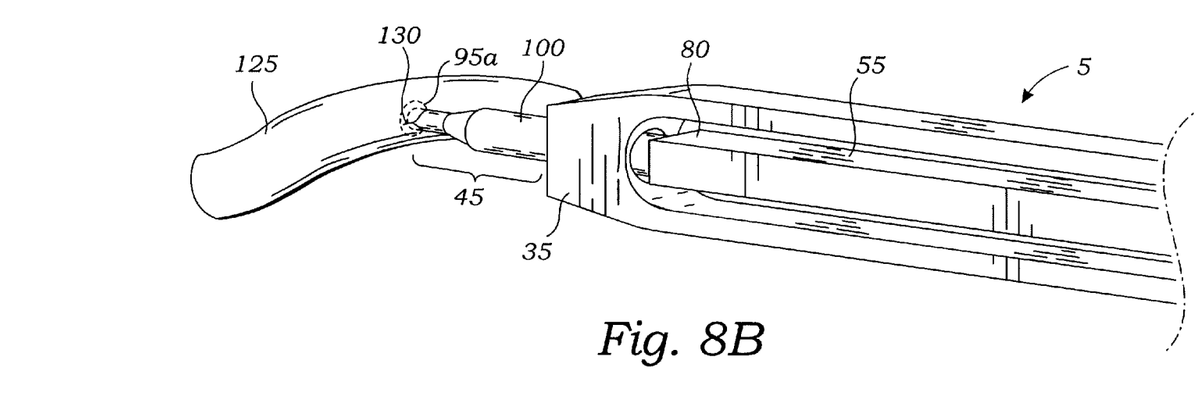
FIG. 8B shows the actuating handle and surgical component of FIG. 8A with the guiding component in an extended position, and a portion of the surgical component inserted into the vessel of FIG. 8A.
Figure 8C:
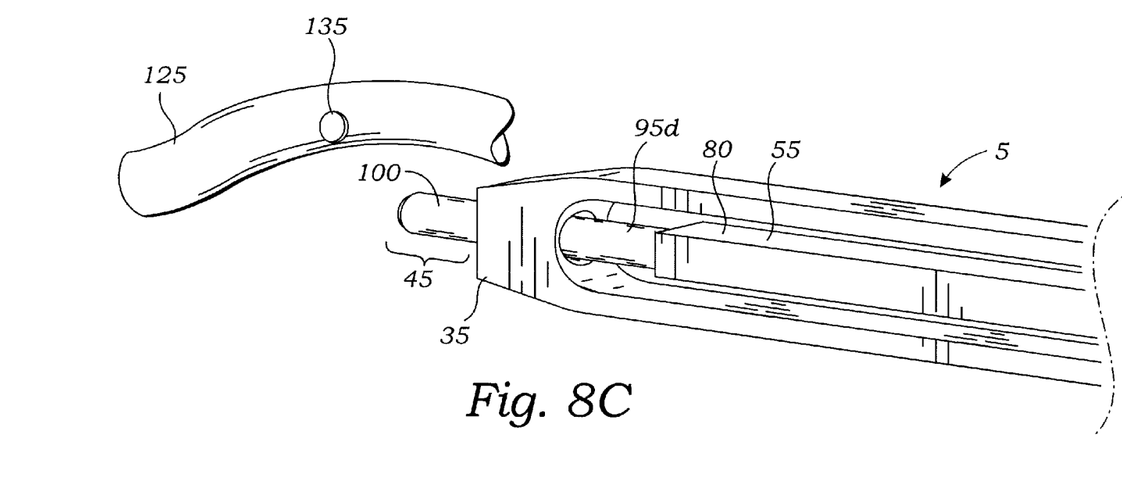
FIG. 8C shows the actuating handle and surgical component of FIG. 8B with the guiding component in a retracted position after the surgical component has been used on the vessel.

Handle 5 may be used for multiple applications, but is especially suited for surgical applications. An example of such use is illustrated in FIGS. 8A–8C, and will be described shortly. Turning first to FIG. 7, a typical surgical component 45 (a vessel punch) will be briefly described. It should be understood that the embodiment of vessel punch 45 in FIG. 7 is for illustration purposes only. Many vessel punch designs are known in the art, and the present invention contemplates use of a wide variety of vessel punches, as well as other surgical components 45.

Non-moveable portion 100 of vessel punch 45 is a cylindrical sleeve. Moveable portion 95 is received within sleeve 100, and includes a circular punch head 95a, a punch neck 95b, conical support 95c, cylinder 95d, tail 95e, and hook 95f. Tail 95e fits into opening 85 at tip 80 of guiding component 55, and is secured in place by friction as well as by hook 95f. Cylinder 95d then extends through sleeve 100, which fits securely into opening 40 at distal tip 35 of neck 30, such that conical support 95c protrudes from sleeve 100, and punch neck 95b along with punch head 95a are exposed. Sleeve 100 is also secured by friction.

Turning now to FIGS. 8A–8C, again using the vessel punch 45 seen in FIG. 7 for illustration purposes, it should be apparent that retraction of guiding component 55 along axis A—A in response to actuation of actuating component 50, with hook 95f secured in guiding component 55, causes moveable portion 95 of vessel punch 45 to retract substantially along axis A—A correspondingly, such that vessel punch 45 may perform its intended operative function of creating a hole in a vessel when punch head 95a traps the tissue to be punched at the opening in sleeve 100.

FIG. 8A shows handle 5 and surgical component 45 in position for use on a vessel 125. Vessel 125 may be an aorta or other vessel. An initial opening 130 such as an incision is created in vessel 125, using well-known methods. The width of incision 130 should be slightly less than the width of punch head 95a, so the portion of vessel 125 containing the initial incision 130 will be completely removed by punch head 95a, resulting in a punch hole 135 (FIG. 8C). FIG. 8A corresponds to FIG. 5, in which guiding component 55 is in an extended position, and moveable portion 95 of vessel punch 45 is correspondingly initially extended, both due to bias of spring force component 70. A surgeon may be gripping handle 5 as seen in FIG. 5, in preparation for retracting moveable portion 95 of vessel punch 45. Handle 5 may accommodate alternate gripping styles as well, such as placing the thumb, rather than the padded portion of the palm, into indented back portion 140 of heel 115.

To perform the desired function, in this example punching a hole 135 in vessel 125, the surgeon inserts an operative portion of surgical component 45 into incision 130. This is seen in FIG. 8B, in which the operative portion of surgical component 45 is punch head 95a. Typically, the surgeon allows guiding component 55 and moveable portion 95 of vessel punch 45 to remain in a fully extended position while inserting punch head 95a to a desired depth, such as a few millimeters.

Once punch head 95a is in place, the surgeon actuates actuating component 50 by manipulating finger grip 65 in a direction to oppose the natural bias force of spring force component 70, causing spring force component 70 to compress, and causing guiding component 55 and moveable portion 95 of surgical component 45 to correspondingly retract substantially along longitudinal axis A—A such that surgical component 45 performs the desired operative function. In the example described herein, the desired function is punching vessel 125, to create punch hole 135 for allowing access into vessel 125 of surgical or diagnostic instruments, or implantation of bioprosthetic devices, or to create an attachment point for autologous or xenographic tissues. The result is seen in FIG. 8C, which corresponds to FIG. 6 in which spring force component 70 is compressed, and guiding component 55 and moveable portion 95 of vessel punch 45 are correspondingly retracted. After the desired function is performed, the surgeon may typically release pressure on finger grip 65 to allow spring force component 70 to decompress, or return to its natural bias position.

Handle 5 may be designated for single use only, but the material properties of handle 5 (e.g., material used, overall dimensions, radii 105 associated with spring force component 70, effect of stress limiting component 110), are preferably chosen to increase reliability of handle 5 for multiple uses. The single-piece construction of handle 5 decreases the complexity of manufacture and maintenance. Ergonomic finger grip 65 contributes to a secure and comfortable grip, and allows for controlled actuation of actuating component 50 with only a single hand. Handle 5 may be manufactured in various dimensions as necessary for a particular function, but a single handle 5 may be adapted to receive a variety of surgical components 45.

While certain embodiments are illustrated in the drawings and are described herein, including preferred embodiments, it will be apparent to those skilled in the art that the specific embodiments described herein may be modified without departing from the inventive concepts described. For example, the specific shapes and dimensions of handle 5 may vary according to need, as can the location of stress limiting component 110. Various metal, plastic, or other suitable materials may be used to manufacture handle 5, and various methods of attachment of surgical component 45 to guiding component 55 may be used. Accordingly, the invention is not to be restricted except by the claims which follow.

What is claimed is:

1. A single-piece actuating handle for actuating a surgical component comprising:
    an outer portion comprising a head and a neck, the neck having a distal tip; and
    an inner portion comprising an actuating component and a guiding component;
    wherein the inner portion is positioned substantially within the outer portion;
    wherein the inner portion merges into the outer portion at a first merge location;
    wherein the guiding component merges into the actuating component at a second merge location;
    wherein the guiding component has a distal tip adapted to receive a surgical component;
    wherein the actuating component comprises a finger grip and a spring force component;
    wherein the finger grip merges into the spring force component at a third merge location;
    wherein the spring force component is biased to force the guiding component towards the distal tip of the neck.

2. The single-piece handle of claim 1, wherein the first merge location and the third merge location define opposing terminal ends of the spring force component.

3. The single-piece handle of claim 2, wherein the handle further comprises a stress limiting component positioned to limit stress at a critical point of the spring force component by limiting movement of the spring force component at the critical point during actuation of the actuating component such that a radius of curvature associated with the critical point does not reach a critical radius.

4. The single-piece handle of claim 3, wherein the stress limiting component protrudes from the finger grip and contacts the spring force component at a position of maximum actuation.

5. The single-piece handle of claim 4, in combination with a surgical component attached to the distal tip of the guiding component.

6. The single-piece handle of claim 5, wherein the surgical component extends through an opening at the distal tip of the neck.

7. The single-piece handle of claim 5, wherein the surgical component is a cardiovascular punch.

8. The single-piece handle of claim 1, in combination with a surgical component attached to the distal tip of the guiding component, wherein the surgical component extends through an opening at the distal tip of the neck.

9. The single-piece handle of claim 8, wherein the surgical component is a cardiovascular punch.

10. The single-piece handle of claim 1, wherein the handle is machined from a single block of material.

11. The single-piece handle of claim 1, wherein the handle is molded from a single mold cavity.

12. The single-piece handle of claim 1, wherein the handle is cast from a single mold.

13. The single-piece handle of claim 1, wherein the handle is stamped from a single sheet of metal.

14. The single-piece handle of claim 1, wherein the distal tip of the guiding component is substantially within the neck.

15. A single-piece actuating handle for actuating a surgical component comprising:
    an outer portion comprising a head and a neck; and
    an inner portion comprising an actuating component and a guiding component;
    wherein the inner portion merges into the outer portion at a first merge location, and comprises a spring force component and a finger grip;
    wherein the guiding component is adapted to receive a surgical component on a distal tip thereof and is aligned along a longitudinal axis of the neck, and is connected to the actuating component at a second merge location such that actuation and release of the actuating component each cause the guiding component to move longitudinally substantially along the axis in retracted and extended directions respectively.

16. The single-piece handle of claim 15, further comprising a stress limiting component positioned to limit stress at a critical point of the spring force component by limiting movement of the spring force component at the critical point during actuation of the actuating component such that a radius of curvature associated with the critical point does not reach a critical radius.

17. The single-piece handle of claim 15, in combination with a surgical component extending through an opening at a distal tip of the neck and attached to the distal tip of the guiding component wherein a moveable portion of the surgical component moves in synch with the guiding component substantially along the axis upon actuation and release of the actuating component.

18. The single-piece handle of claim 17, wherein the surgical component is a cardiovascular punch.

19. The single-piece handle of claim 15, wherein the handle is machined from a single block of material.

20. The single-piece handle of claim 15, wherein the handle is molded from a single mold cavity.

21. The single-piece handle of claim 15, wherein the handle is cast from a single mold.

22. The single-piece handle of claim 15, wherein the handle is stamped from a single sheet of metal.

23. A method of using a surgical instrument comprising the steps:
providing a single-piece actuating handle comprising an outer portion and an inner portion, the inner portion being positioned substantially within the outer portion and merging into the outer portion at a first merge location, the outer portion comprising a head and a neck, the inner portion comprising an actuating component connected to a guiding component, the actuating component comprising a finger grip connected to a spring force component, a surgical component being attached to a distal tip of the guiding component and extending through an opening at a distal tip of the neck;
inserting a moveable portion of the surgical component into an opening in a vessel;
actuating the actuating component by manipulating the finger grip in a direction to oppose a natural bias force of the spring force component, causing the spring force component to compress, and causing the guiding component and the moveable portion of the surgical component to retract substantially along a longitudinal axis of the neck such that the surgical component performs an operative function.

24. The method of claim 23, further comprising the step of releasing the finger grip to allow the spring force component to return to a natural bias position.

25. The method of claim 23, wherein the actuating component further comprises a stress limiting component which limits movement of the spring force component at a critical point during actuation of the actuating component such that a radius of curvature associated with the critical point does not reach a critical radius.

26. The method of claim 25, wherein the surgical component is a cardiovascular punch, and wherein the operative function is creating a punch hole in the vessel.

27. The method of claim 23, further comprising the step of creating the opening in the vessel.

28. The method of claim 23, wherein the surgical component is a cardiovascular punch, and wherein the operative function is creating a punch hole in the vessel.

29. The method of claim 23, wherein the actuating step occurs after the insertion step.

\* \* \* \* \*